United States Patent [19]

InDelicato et al.

[11] Patent Number: 5,357,985
[45] Date of Patent: Oct. 25, 1994

[54] SYSTEM AND METHOD FOR APPLYING A PROTECTIVE COATING AND/OR EXTENSIONS TO FINGERNAILS

[76] Inventors: Len InDelicato, 18080 Boris Dr., Encino, Calif. 91436; George H. Carroll, 2392 Foster Ave., Ventura, Calif. 93001

[21] Appl. No.: 107,629

[22] Filed: Aug. 18, 1993

[51] Int. Cl.$^5$ .................................. A45D 24/00
[52] U.S. Cl. .................................. 132/200; 132/73; 132/73.5
[58] Field of Search ............. 132/73, 73.5, 74.5, 132/200; 424/61, 78.03, 78.31

[56] References Cited

U.S. PATENT DOCUMENTS

| | | | |
|---|---|---|---|
| 3,285,256 | 11/1966 | Despard | 132/74.5 |
| 3,480,020 | 11/1969 | Ernest | 132/74.5 |
| 4,222,399 | 9/1980 | Ionescu | 132/73 |
| 4,626,428 | 12/1986 | Weisberg et al. | 424/61 |
| 4,627,453 | 12/1986 | Isler | 132/73 |
| 4,646,765 | 3/1987 | Cooper et al. | 132/73 |
| 4,687,827 | 8/1987 | Russo | 132/73 |
| 4,704,303 | 11/1987 | Cornell | 424/61 |
| 4,724,177 | 2/1988 | Russo | 132/73 |
| 4,844,102 | 7/1989 | Repensek et al. | 132/73 |
| 5,209,250 | 5/1993 | Taeckens | 132/200 |

*Primary Examiner*—Gene Mancene
*Assistant Examiner*—Frank A. LaViola
*Attorney, Agent, or Firm*—Dennis H. Lambert

[57] ABSTRACT

A simplified system and method of applying protective coatings and/or extensions to fingernails, wherein a quantity of cyanoacrylate gel is applied to the fingernail surface from the discharge nozzle of a squeeze bottle, and the nozzle is used to spread and smooth the gel uniformly over the fingernail surface. A drop of hardener is then applied from the discharge nozzle of a squeeze bottle onto the center of the layer of gel, from whence the hardener rapidly spreads over the entire surface of the layer of gel, curing and hardening the gel.

5 Claims, 2 Drawing Sheets

SYSTEM AND METHOD FOR APPLYING A PROTECTIVE COATING AND/OR EXTENSIONS TO FINGERNAILS

TECHNICAL FIELD

This invention relates to fingernail extension and repair systems, and especially to a system and method for applying a protective coating and/or extension to fingernails.

BACKGROUND OF THE INVENTION

A variety of systems have been developed for the repair and cosmetic enhancement of fingernails, including the use of artificial fingernails. The most successful and popular systems employ a cyanoacrylate gel which is spread over the surface of the fingernail and cured to form a protective coating or to adhesively secure an artificial fingernail to the natural nail. Such systems have been developed which use powders and liquids that are blended and applied to the fingernail surface to form a gel that hardens, or to cyanoacrylate liquids or gels contained in bottles for application to the fingernail by use of a brush or the like. Separate accelerators or hardeners to cure the gel are then applied by spraying or brushing the hardener onto the previously applied layer of cyanoacrylate gel. In all such systems, paramount considerations are ease of use, absence of toxicity and appearance of the finished product.

Examples of several prior art systems are described in U.S. Pat. Nos. 4,626,428, 4,627,453, 4,646,765, 4,724,177 and 4,687,827.

U.S. Pat. No. 4,626,428 discloses a process for applying an acrylic coating to a fingernail, in which a powdered polymethacrylate ester is applied to a nail surface wetted with a slow curing cyanoacrylate glue, a blend of acrylic monomers is brushed onto the applied powder and glue, and the nail is finished after curing of the glue.

U.S. Pat. No. 4,627,453 teaches a system for forming an artificial fingernail from layers of organic fabric, such as silk, applied over a natural nail with adhesive and hardened with a hardening solution.

U.S. Pat. No. 4,646,765 describes a system in which a mixture of cyanoacrylate and graphite fibers is applied to a fingernail and cured by spraying a hardener/accelerator onto the cyanoacrylate compound.

U.S. Pat. No. 4,724,177 is directed to a package for applying cyanoacrylate to a fingernail. In this system, a brush prewetted with a solvent for the cyanoacrylate is immersed in a bottle of the cyanoacrylate and used to brush it onto a nail surface. Thereafter, an accelerator is sprayed onto the cyanoacrylate to cure it.

U.S. Pat. 4,687,827 is directed to the method of applying cyanoacrylate as defined in U.S. Pat. No. 4,724,177.

In all of the prior art systems known to applicant, considerable skill is required to apply the cyanoacrylate and hardener so that a smooth and unblemished surface results. Moreover, many prior art systems require several steps and involve the use of many components, which adds to the difficulty of using the systems and increases their cost. Use of a brush to apply the cyanoacrylate or hardener may result in brush marks in the cyanoacrylate, which must be buffed out. Further, in those systems utilizing a container of cyanoacrylate gel or liquid having a brush or the like apply the gel to the fingernail surface, or to a hardener which is applied by brush or the like, there exists the potential for accidentally tipping over the container while the brush, etc. is out of the bottle, thereby tipping over and spilling the gel or hardener.

In those systems using a spray applicator to apply the hardener, the danger of tipping over an open bottle of hardener is eliminated, but disadvantages are introduced associated with the use of sprays.

Accordingly, there is need for a simple and inexpensive system and method for applying a protective coating or fingernail extension using a cyanoacrylate gel and hardener, wherein the danger of accidentally tipping over an open container of gel or hardener is minimized, and the application of the gel and hardener is reduced to a minimum number of steps, while at the same time a smooth finish is achieved without the need for excessive grinding and buffing.

Where reference herein is made to fingernails, it is to be understood that the invention applies equally as well to toenails, or to other surfaces, and use of the invention for such other applications is also intended to be covered.

DISCLOSURE OF THE INVENTION

A simplified system and method of applying protective coatings and/or extensions to fingernails is provided in accordance with the present invention, wherein a quantity of cyanoacrylate gel is applied to the fingernail surface from the discharge nozzle of a squeeze bottle, and the nozzle is used to spread and smooth the gel uniformly over the fingernail surface. A drop of hardener is then applied from the discharge nozzle of a squeeze bottle into the center of the layer of gel, from whence the hardener rapidly spreads over the entire surface of the layer of gel, promoting hardening of the gel.

Separate brushes and the like are not required, and the resulting finish is smooth and uniform without the need for excessive grinding and buffing.

The viscosity of the cyanoacrylate gel is selected so that it does not flow uncontrollably from the fingernail surface, but yet is such that the gel can be easily spread over the surface of the nail with the applicator tip and will settle to a smooth, uniform finish. In most cases, the gel used in the system of the invention has a higher viscosity than the gel used in prior art systems.

The use of only two essentially identical containers for applying both the gel and the hardener reduces the cost of the system and makes it easier and more simple to use. At the same time, during application of the gel or hardener to a surface there are not any open containers of gel or hardener sitting around which may be accidentally tipped over and their contents spilled. Additionally, elimination of an open container of accelerator reduces the amount of airborne fumes which would otherwise be discharged into the atmosphere with a conventional system.

BRIEF DESCRIPTION OF THE DRAWINGS

The foregoing, as well as other objects and advantages of the invention, will become apparent from the following detailed description when considered in conjunction with the accompanying drawings, wherein like reference characters designate like parts throughout the several views, and wherein.

DETAILED DESCRIPTION OF THE PREFERRED EMBODIMENTS

Figure 1:
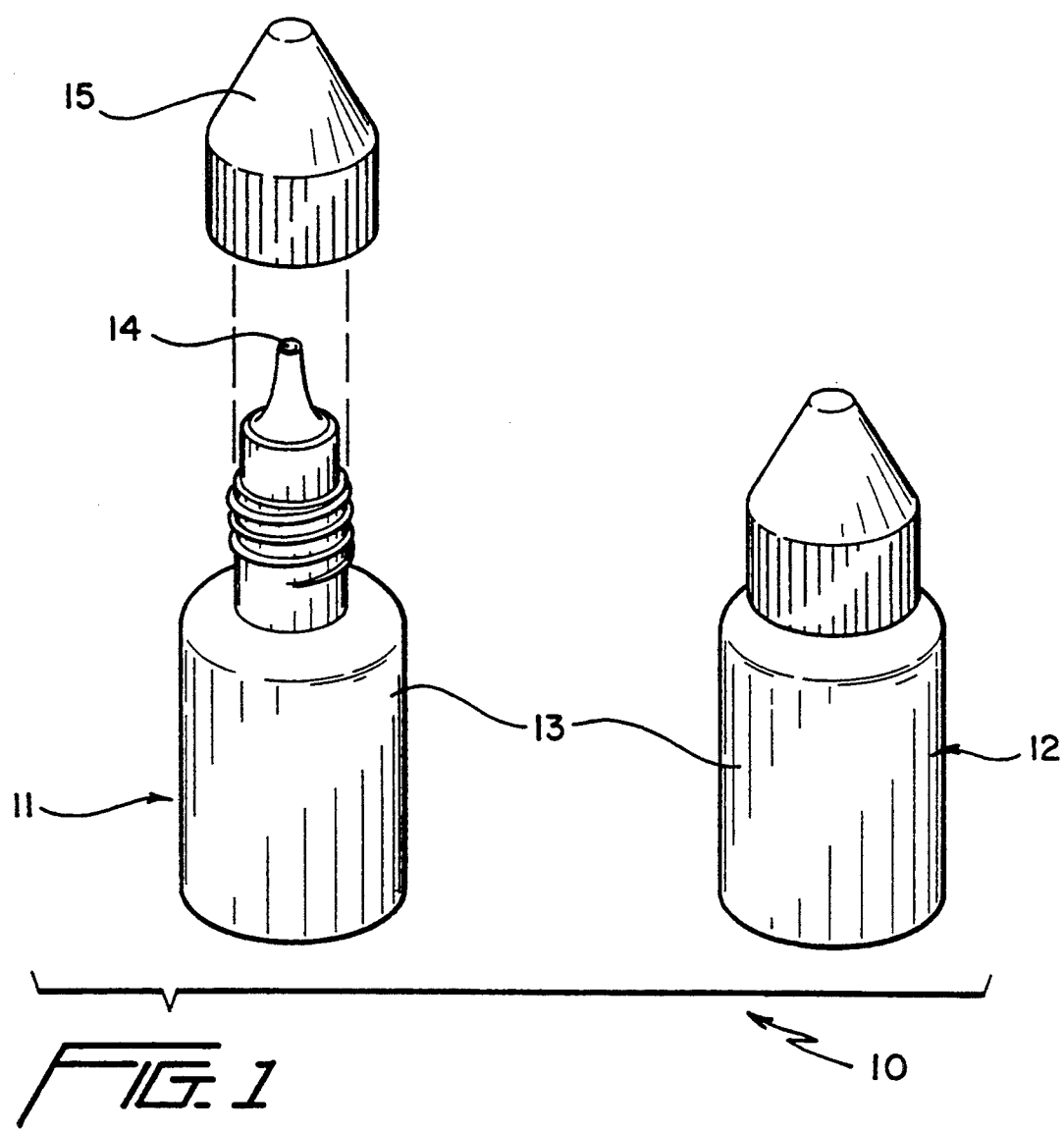
FIG. 1 is an exploded perspective view of a system according to the invention, including a pair of squeeze bottles for containing and dispensing the cyanoacrylate gel and the accelerator for the gel, with one of the bottles having its closure cap removed.

Referring more specifically to the drawings, a system in accordance with the invention is represented generally at 10 in FIG. 1. The system includes a container 11 of cyanoacrylate gel and a container 12 of an accelerator/hardener for the gel. In the form shown, each container comprises a squeezable plastic bottle 13 having an elongate discharge nozzle 14 and a closure cap 15 for threaded engagement on the bottle. The bottle and cap for containing the cyanoacrylate gel are preferably made of a material to which the gel does not adhere, such as high density polyethylene (HDPE) or Teflon, for example. In the preferred embodiment, the containers are identical to one another, although they may be different from one another if desired.

The cyanoacrylate may be selected from any of a variety of suitable cyanoacrylate compounds having a viscosity in the range of from about 500 centipoise to about 2,500 centipoise, and preferably from about 800 to about 2,000 centipoise. It has been found that in this viscosity range the gel does not flow uncontrollably from the nail surface, but it does spread easily by use of the nozzle of the squeeze bottle and it quickly flows or settles into a smooth, uniform surface. The viscosity of the gel may be adjusted by adding thickening agents or plasticizers, depending upon the desired characteristics of the gel. Suitable plasticizers may include esters of cyanoacetic acid, succinic acid, glycerine triacetate and glycerine tributyrate. Suitable thickeners include polymethyl methacrylate, polyacrylates, polymethacrylates, cellulose acetates and similar cellulose esters as well as other polymer materials.

The accelerator/hardener may comprise any of a number of suitable base chemicals, including, but not limited to, ammonia, amine, or a mixture of trichlorotrifluoroethane and a methylaniline such as N,N-dimethyl-P-toluidine, or other organic base.

Figure 2:
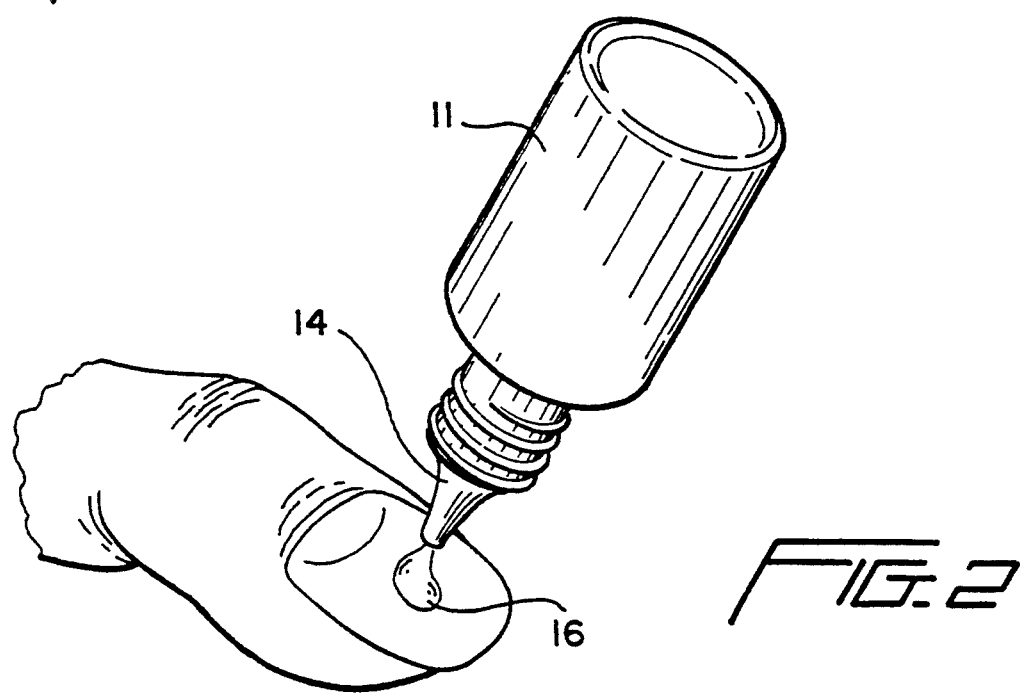
FIG. 2 is a perspective view showing how a quantity of the gel may be dispensed from its container onto a fingernail surface.
Figure 3:
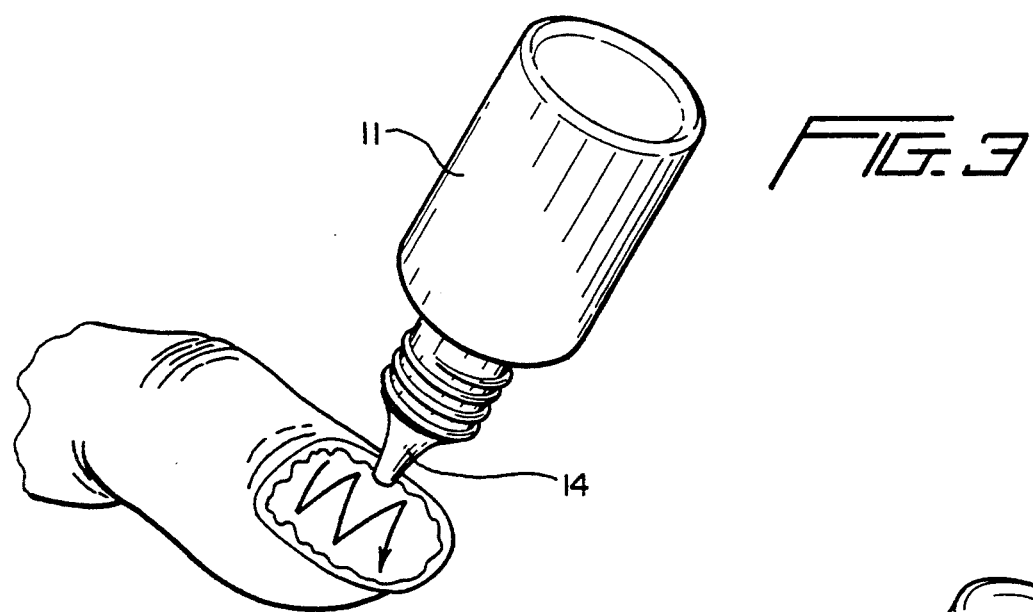
FIG. 3 is a perspective view showing how the nozzle of the gel container may be manipulated to spread the gel around evenly over the fingernail surface.
Figure 4:
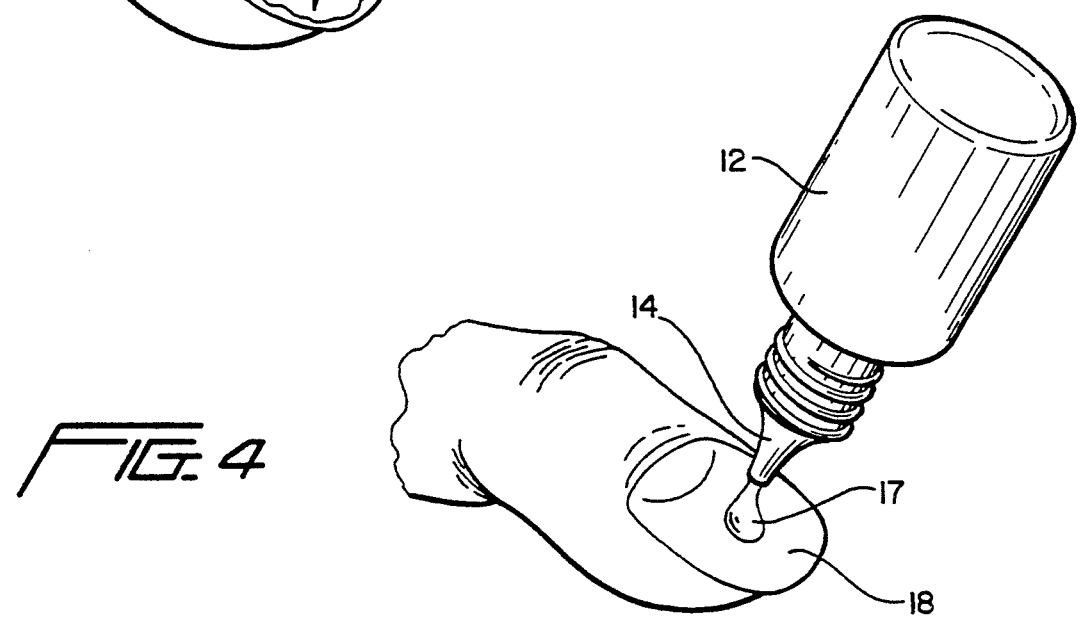
FIG. 4 is a perspective view showing how a drop of the accelerator for the cyanoacrylate is applied from its container onto the center of the surface of the previously applied layer of cyanoacrylate gel.
Figure 5:
FIG. 5 is a schematic perspective view showing how the drop of accelerator rapidly spreads in all directions over the entire surface of the gel, resulting in rapid and uniform curing of the gel to form a smooth finish without requiring excessive grinding and buffing.

In use, all polish is first removed from the fingernails and the hands and nails are washed thoroughly. The nails are then buffed lightly and a thin layer of the cyanoacrylate gel is applied over the surface of the nail by squeezing a drop 16 of the gel onto the center of the nail from the container and then spreading the gel evenly over the nail surface using the nozzle tip (see FIGS. 2 and 3). Thereafter, a drop 17 of the accelerator/hardener is squeezed onto the center of the gel surface 18, and almost instantly flows outwardly to cover the entire surface of the cyanoacrylate, causing it to cure rapidly and uniformly. The resultant finish is smooth and free of ridges, brush marks and similar imperfections, thereby requiring a minimum of buffing in order to achieve the desired appearance.

While the invention has been illustrated and described in detail herein, it is to be understood that various modifications may be made therein without departing from the spirit and scope of the invention, as defined by the appended claims.

What is claimed is:

1. A method for applying cyanoacrylate to fingernails, comprising the steps of:

applying a quantity of cyanoacrylate gel directly from a container of the gel through an applicator tip on the container to the upper surface of the fingernail;

using the applicator tip on the container of cyanoacrylate gel to spread and smooth the applied quantity of cyanoacrylate gel on the upper surface of the fingernail;

applying a quantity of accelerator directly from a container of the accelerator through an applicator tip of the container to the cyanoacrylate gel previously applied to the fingernail; and permitting the accelerator to disperse unaided over the surface of the cyanoacrylate gel to promote rapid and uniform curing of the cyanoacrylate gel.

2. A method as claimed in claim 1, wherein:

the containers of gel and accelerator both comprise squeeze bottles, and the container of accelerator is squeezed to dispense a drop of accelerator through the applicator tip to approximately the center of the upper surface of cyanoacrylate gel previously applied to the nail.

3. A kit for applying cyanoacrylate to fingernails to form a protective coating on the fingernail or to cosmetically enhance the fingernail, comprising, in combination:

a first squeeze bottle container holding a quantity of cyanoacrylate gel having a predetermined viscosity for controlled flowability of the gel, said first container having an applicator tip through which the gel is dispensed directly onto the upper surface of the fingernail;

said applicator tip comprising a spreading implement for spreading the cyanoacrylate gel over the upper surface of the fingernail; and a second squeeze bottle container holding a quantity of accelerator for the cyanoacrylate gel, said second container having an applicator tip through which at least one drop of the accelerator is dispensed onto the previously applied cyanoacrylate gel to cure and harden the cyanoacrylate gel.

4. A system as claimed in claim 3, wherein:

the first and second containers are identical to one another, except that one contains a cyanoacrylate gel and the other contains an accelerator for the cyanoacrylate gel.

5. A system as claimed in claim 3, wherein:

the cyanoacrylate gel has a viscosity of about 1500 centipoise.

* * * * *